(12) United States Patent
Cleveland et al.

(10) Patent No.: US 7,484,880 B2
(45) Date of Patent: Feb. 3, 2009

(54) VORTEX STIRRING OF VESSELS IN A TWO-DIMENSIONAL ARRAY

(75) Inventors: Patrick H. Cleveland, Rancho Santa Fe, CA (US); Timothy Michael Doht, San Diego, CA (US)

(73) Assignee: V & P Scientific, Inc., San Diego, CA (US)

( * ) Notice: Subject to any disclaimer, the term of this patent is extended or adjusted under 35 U.S.C. 154(b) by 692 days.

(21) Appl. No.: 11/166,831

(22) Filed: Jun. 24, 2005

(65) Prior Publication Data

US 2008/0205190 A1    Aug. 28, 2008

(51) Int. Cl.
B01F 13/08 (2006.01)
(52) U.S. Cl. ...................................... 366/273
(58) Field of Classification Search ............... 366/273, 366/274
See application file for complete search history.

(56) References Cited

U.S. PATENT DOCUMENTS

| | | | | |
|---|---|---|---|---|
| 3,356,346 | A * | 12/1967 | Landsberger | 366/274 |
| 3,601,372 | A * | 8/1971 | Harmes | 366/274 |
| 4,040,605 | A * | 8/1977 | Towsend | 366/273 |
| 4,390,283 | A * | 6/1983 | Meyer | 366/273 |
| 4,876,069 | A * | 10/1989 | Jochimsen | 366/273 |
| 4,911,555 | A | 3/1990 | Saffer et al. | |
| 4,925,629 | A | 5/1990 | Schramm | |
| 5,272,092 | A * | 12/1993 | Hamasaki et al. | 366/273 |
| 5,529,391 | A * | 6/1996 | Kindman et al. | 366/145 |
| 6,176,609 | B1 | 1/2001 | Cleveland et al. | |
| 6,357,907 | B1 | 3/2002 | Cleveland | |
| 6,382,827 | B1 * | 5/2002 | Gebrian | 366/274 |
| 2002/0118594 | A1 | 8/2002 | Vellinger | |

FOREIGN PATENT DOCUMENTS

| | | |
|---|---|---|
| DE | 33 44 754 A1 | 6/1985 |
| DE | 298 19 380 U1 | 2/1999 |

* cited by examiner

*Primary Examiner*—Tony G Soohoo
(74) *Attorney, Agent, or Firm*—Edward W. Callan

(57) ABSTRACT

The contents of a two-dimensional array of vessels are mixed by a vortex created by continuous lateral tumbling of a magnetic stir element against the interior side wall of each vessel. The system includes a drive magnet having oppositely polarized sides, and a carousel including receptacles at different heights and at different positions about the carousel's axis of rotation for receiving a plurality of arrays of vessels. The magnet's vertical physical axis is aligned with the carousel's axis of rotation so that the magnet is disposed to one side of each of the receptacles. The magnet provides magnetic flux lines that rotate horizontally through 360 degrees within the received vessels when the magnet is rotated about its vertical physical axis to thereby cause magnetic stir elements in the vessels to continuously tumble laterally against the interior side wall of the vessel and thereby create the vortexes.

23 Claims, 5 Drawing Sheets

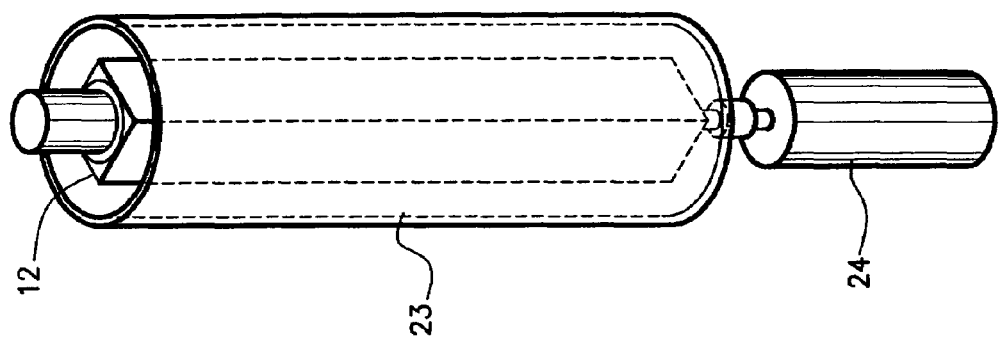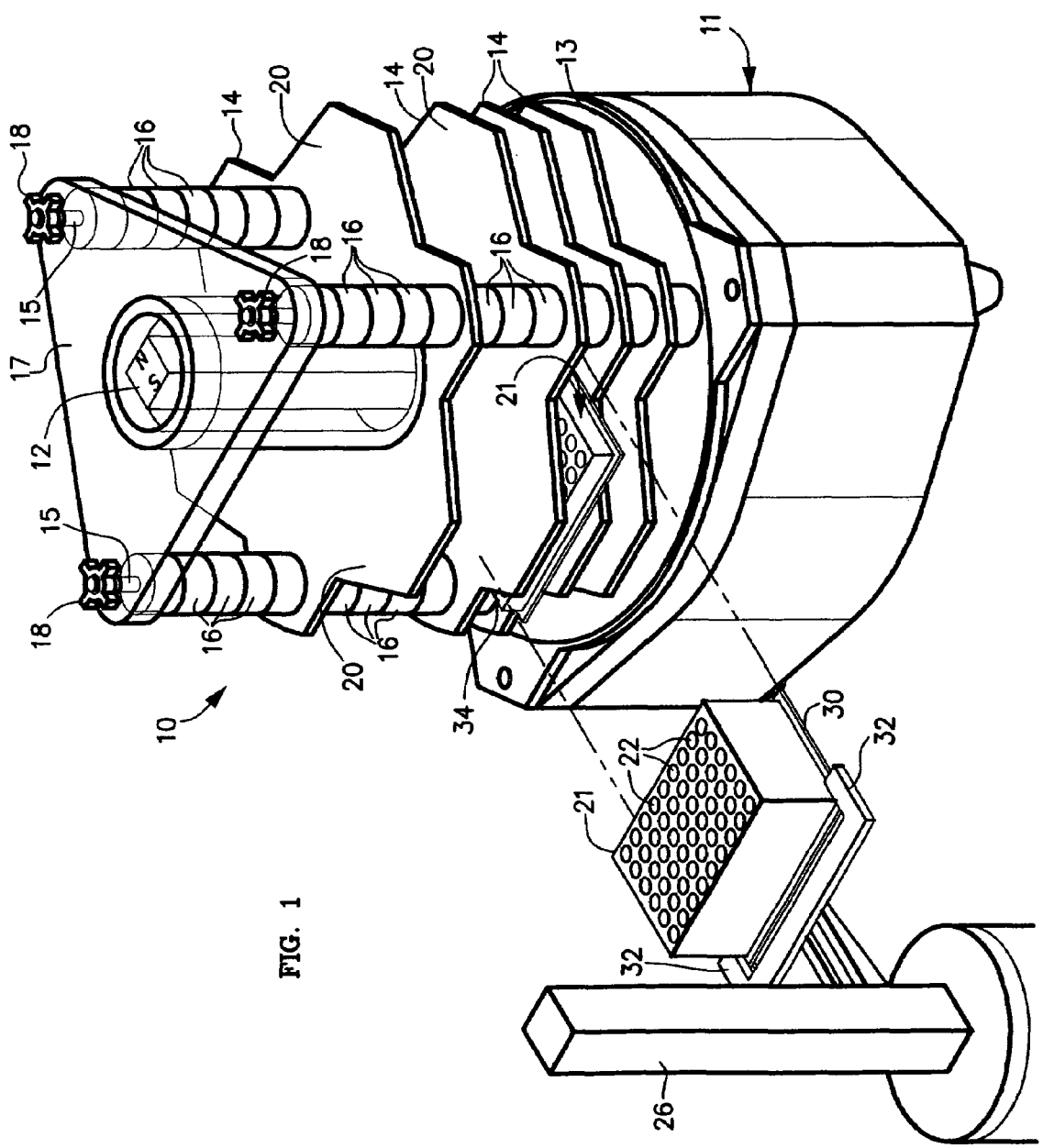

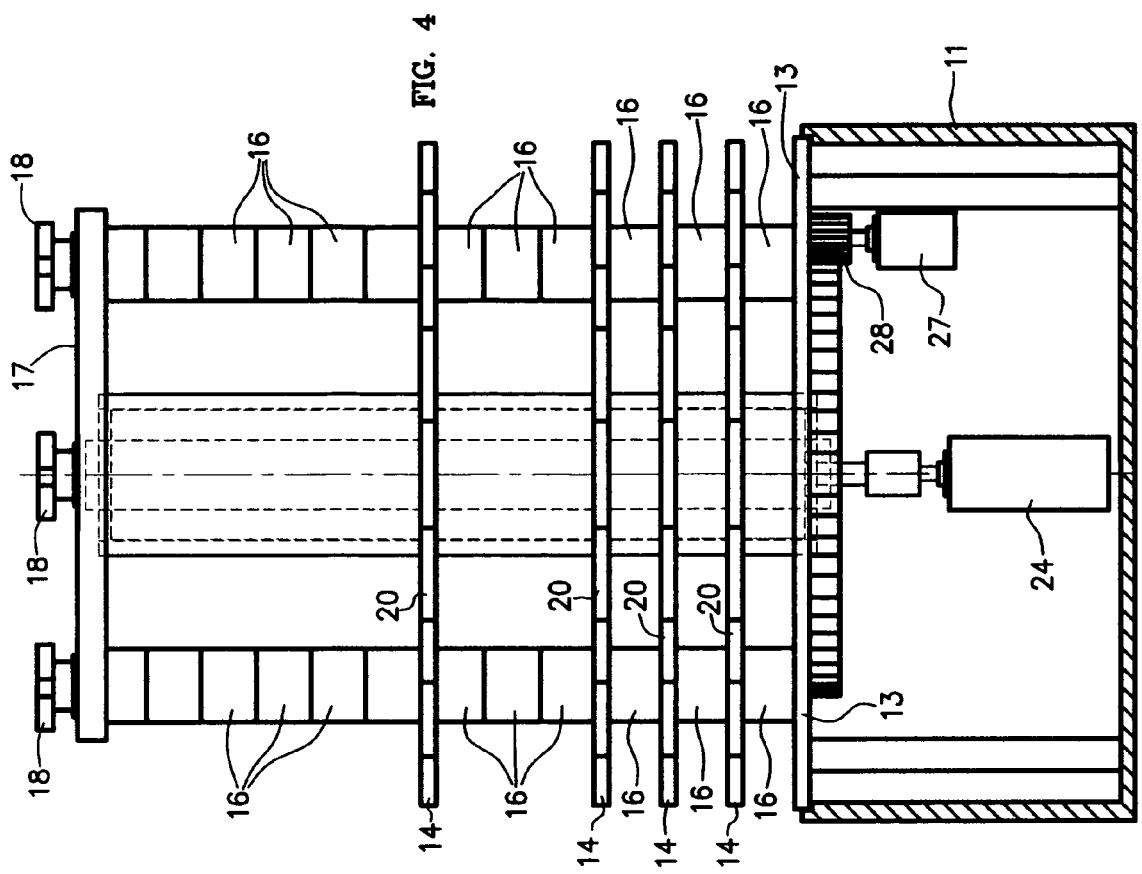
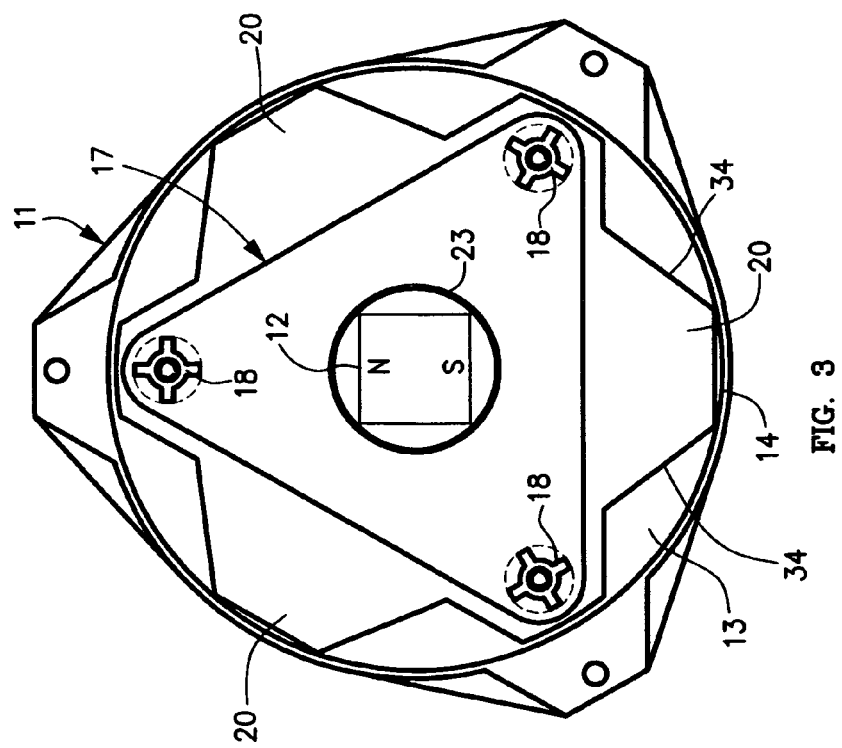

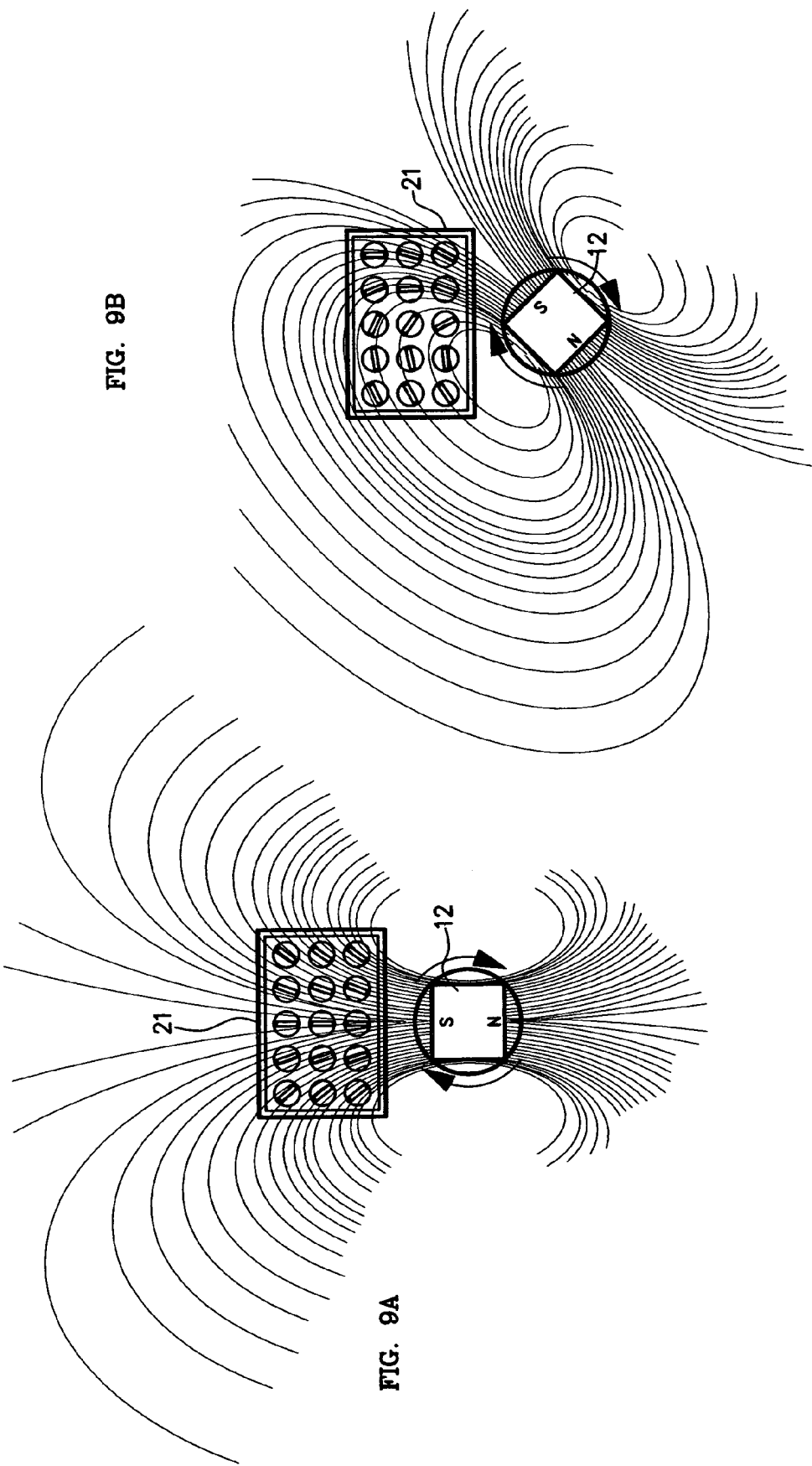

US 7,484,880 B2

VORTEX STIRRING OF VESSELS IN A TWO-DIMENSIONAL ARRAY

BACKGROUND OF THE INVENTION

The present invention generally pertains to mixing the contents of a two-dimensional array of vessels and is particularly directed to mixing such contents by causing magnetic stir elements within the vessels to tumble in response to the rotation of magnetic flux lines.

In a prior art magnetic tumble stirring apparatus, which is described in U.S. Pat. No. 6,176,609 to Cleveland and Markle, a two-dimensional array of vessels which contain magnetic stir elements is disposed above a rotatable permanent magnet that is disposed to have its physical axis of rotation in a horizontal plane and a magnetic-flux axis in a vertical plane. Rotation of the permanent magnet causes the magnetic flux lines emanating from the magnet to rotate through 360 degrees in the vertical plane within the vessels to thereby cause the magnetic stir elements in the vessels to tumble and thereby mix the contents of the vessels.

In prior art systems in which the contents of a two-dimensional array of vessels are mixed by a vortex created by continuous lateral tumbling of a magnetic stir element within each vessel, a magnetic drive that provides magnetic flux lines of varying orientation to thereby cause the tumbling of the stir elements is positioned beneath each vessel. These systems are impractical for stirring the contents of a large array of vessels that are embodied as wells in a microplate.

SUMMARY OF THE INVENTION

The present invention provides a system for mixing the contents of a two-dimensional array of vessels containing magnetic stir elements, wherein each vessel has a vertical axis as defined when the vessel is disposed for the mixing of said contents, the system comprising: means for receiving at least one array of vessels in a disposition for the mixing of said contents; a drive magnet for providing magnetic flux lines; and means for causing the magnetic flux lines to rotate through 360 degrees; wherein the drive magnet is disposed for causing the magnetic flux lines to rotate horizontally through 360 degrees within vessels received by the receiving means to thereby cause the magnetic stir elements in the received vessels to continuously revolve around the vertical axis of the vessel and while so revolving to continuously tumble laterally against the side wall of the vessel whereby the contents of a said vessel containing a said magnetic stir element are mixed by a vortex created by the continuous lateral tumbling of the stir element against the side wall of the vessel.

The term "lateral" is defined as "of, at, from or toward the side".

The present invention also provides a method of mixing the contents of a two-dimensional array of vessels containing magnetic stir elements, wherein each vessel has a vertical axis as defined when the vessel is disposed for the mixing of said contents, the method comprising the steps of:

(a) receiving at least one array of vessels in a disposition for the mixing of said contents; and (b) causing magnetic flux lines to rotate horizontally through 360 degrees within the received vessels to thereby cause the magnetic stir elements in the received vessels to continuously revolve around the vertical axis of the vessel and while so revolving to continuously tumble laterally against the side wall of the vessel; whereby the contents of a said vessel containing a said magnetic stir element are mixed by a vortex created by the continuous lateral tumbling of the stir element against the side wall of the vessel.

In contrast lateral tumble stirring against the sidewall of the vessel, as provided by the present invention, the above-described prior art magnetic tumble stirring apparatus causes the stir element to tumble against the bottom of vessel. Tumble stirring against the sidewall of the vessel has the advantage of creating a vortex that results in better mixing of the contents of a tall vessel. In addition, the present invention does not require a magnetic-field axis-of-rotation beneath each vessel for efficient mixing, as does the above-described prior art magnetic tumble stirring apparatus.

Additional features of the present invention are described with reference to the detailed description of the preferred embodiments.

BRIEF DESCRIPTION OF THE DRAWING

FIG. 1 is a perspective view of a preferred embodiment of a mixing system according to the present invention in combination with an array of vessels that are being transported by a robotic device for reception by the mixing system.

FIG. 2 is a perspective view of a rotatable permanent magnet device that is included in the preferred embodiment of the mixing system shown in FIG. 1.

FIG. 3 is a top view of the mixing system of FIG. 1.

FIG. 4 is a side view of the mixing system of FIG. 1.

FIGS. 9A, 9B, 9C and 9D illustrate continuous lateral tumbling of magnetic stir elements of the type illustrated in FIG. 5 or FIG. 6 as magnetic flux lines are rotated in the horizontal plane through 360 degrees within the received vessels

DETAILED DESCRIPTION

Figure 6A:
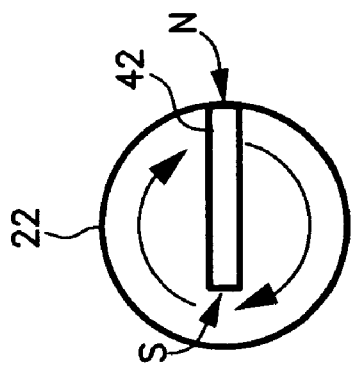
FIGS. 6 and 6A illustrate another type of magnetic stir element within a vessel.

Referring to FIGS. 1, 2, 3 and 4, a preferred embodiment of a mixing system 10 according to the present invention includes a drive magnet 12 and a carousel 13. The carousel 13 includes an assembly for receiving the arrays of vessels. This assembly includes a plurality of shelves 14, three poles 15 that extend vertically through corresponding apertures in the shelves 14; and a number of annular shelf-spacing elements 16 for disposition about the poles 15 above and/or between the shelves 14.

The shelf-spacing elements 16 can be so disposed that the space above one of the shelves 14 can be different than the space above another of the shelves 14. In the preferred embodiment, all of the shelf-spacing elements 16 are of the same predetermined height. In alternative embodiments, some of the shelf-spacing elements are of one height and others of the shelf-spacing elements are of one or more different heights.

After the shelves 14 and shelf-spacing elements 16 have been disposed to provide a set of shelves 14 having preferred amounts of space above the respective shelves 14 in order to accommodate the reception of arrays of vessels of different heights, the poles 15 are secured to a transparent top plate 17.

The tops of each pole 15 are threaded and nuts 18 are screwed onto the threads to secure the poles 15 to the top plate 17.

The plurality of shelves 14 contain a plurality of array-receiving sites 20 disposed at different heights and at different positions about the axis of rotation of the carousel 13. Each array-receiving site 20 is adapted for receiving a two-dimensional array 21 of vessels 22. Each vessel 22 has a vertical axis as defined when the vessel 22 is disposed for the mixing of its contents.

The vertical physical axis of the drive magnet 12 is aligned with the axis of rotation of the carousel 13 so that the drive magnet 12 is disposed horizontally to one side of each of the array-receiving sites 20. In the preferred embodiment the drive magnet 12 is a permanent magnet that is sealed within a cylindrical casing 23, as shown in FIG. 2. Opposite horizontal sides of the permanent magnet 12 are oppositely polarized, as shown in FIG. 3.

The array-receiving sites 20 are vertically disposed at different heights in a direction that is parallel to a vertical physical axis of the drive magnet 12 for receiving a plurality of the arrays 21. The array-receiving sites 20 are also horizontally disposed about the vertical physical axis of the drive magnet 12 for receiving a plurality of the arrays 21 of vessels 22 at different angular positions at at least one of the different heights.

The vertical physical axis of the permanent magnet 12 is elongated to provide a vertically elongated zone of horizontal magnetic flux lines. Such vertically elongated zone approximately coincides with the vertical disposition of the array-receiving sites 20 to thereby provide the magnetic flux lines in the plurality of arrays 21 of vessels 22 received at the different heights.

The permanent magnet 12 is disposed for providing magnetic flux lines that can be caused to rotate horizontally through 360 degrees within the received vessels when the permanent magnet 12 is rotated about its vertical physical axis to thereby cause magnetic stir elements in the received vessels 22 to continuously revolve around the vertical axis of the vessel 22 and while so revolving to continuously tumble laterally against the side wall of the vessel 22. A motor 24 is coupled to the permanent magnet 12 for so rotating the permanent magnet 12.

In an alternative embodiment (not shown), the drive magnet is not a permanent magnet, but instead is an electromagnet that is disposed in the same position as the drive magnet 12 shown in FIG. 1 with its vertical physical axis elongated to provide a vertically elongated zone of horizontal magnetic flux lines that approximately coincides with the vertical disposition of the array-receiving sites 20. The electromagnet is operated to provide magnetic flux lines that rotate horizontally through 360 degrees within the received vessels 22 to thereby cause magnetic stir elements in the received vessels 22 to continuously revolve around the vertical axis of the vessel 22 and while so revolving to continuously tumble laterally against the side wall of the vessel 22.

In both the permanent-magnet embodiment and the electromagnet embodiment, the contents of the vessels 22 containing a magnetic stir element are mixed by the continuous lateral tumbling of the stir element against the side wall of the vessel 22.

An array 21 of vessels 22 may be inserted into a array-receiving site 20 by a robotic device 26. The carousel 13 is mounted in a chassis 11 for rotation about the vertical physical axis of the drive magnet 12 so that a plurality of arrays 21 of vessels 22 can be received respectively by array-receiving sites 20 at different heights from a predetermined rotational position.

The carousel 13 is rotated independently of the drive magnet 12 by a motor 27 and a gear system 28. In the preferred embodiment, the motor and the gear system 28 are adapted for rotating the carousel 13 from one predetermined rotational position at which the arrays 21 of vessels 22 can be received from the robotic device 26 to another such predetermined rotational position, and for maintaining the carousel 13 in the predetermined rotational position to which the carousel 13 has been rotated when the carousel 13 is not being rotated. In alternative embodiments (not shown) the carousel 13 is rotatable by hand and/or is maintained in the rotational position to which the carousel 13 has been rotated by means other than a motor and/or gear system.

The robotic device 26 includes claws 32 that are disposed for gripping opposite sides of a plate 30 that extends outward at the bottom of the array 21 of vessels 22. At each array-receiving site 20, the shelves 14 include tapered sides 34 to facilitate the insertion of an array 21 of vessels 22 onto a shelf 14 by the robotic device 26 without the claws 32 making contact with the shelf 14.

Different types of suitable magnet stir elements are described in the aforementioned U.S. Pat. No. 6,176,609, the disclosure of which is incorporated herein by reference. Stainless steel magnetic stir elements are preferred for cost reasons. Alternatively, stir elements including permanent magnets may be used.

Figure 5:
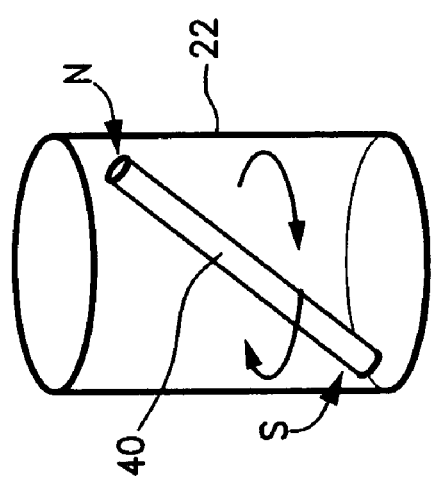
FIG. 5 illustrates one type of magnetic stir element within a vessel.
Figures 9C, 9D:
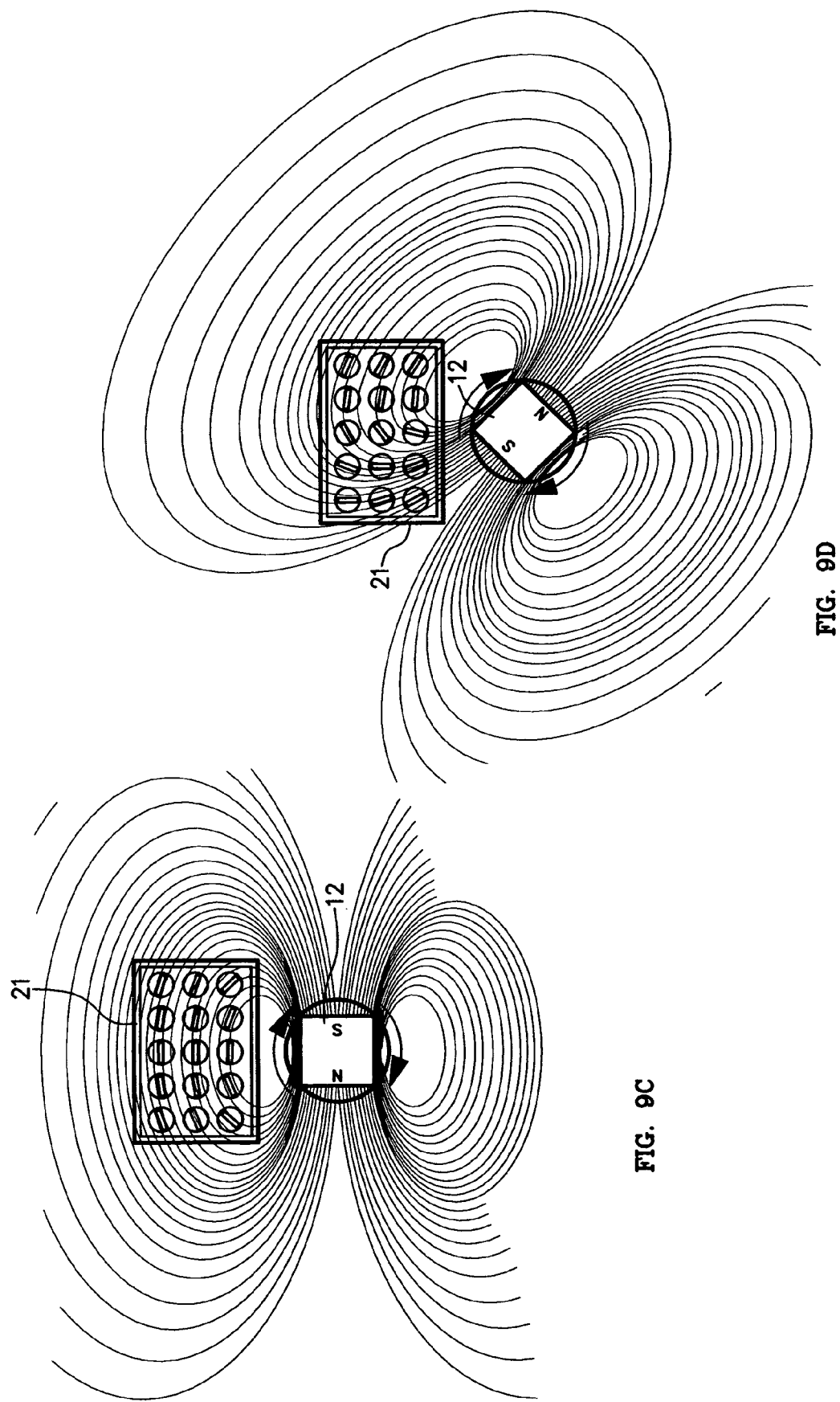

A magnetic stir element 40 of the type shown in FIG. 5 is used with one embodiment of the method of the present invention. The magnetic stir element is a dowel 40 in which the opposite ends thereof are oppositely polarized and the dowel 40 is longer than the internal diameter of the vessel 22. As the magnetic flux lines are rotated horizontally through 360 degrees, the dowel 40 continuously revolves around the vertical axis of the vessel 22 and while so revolving both ends of the dowel 40 laterally tumble against the sidewall of the vessel 22.

Figure 6:
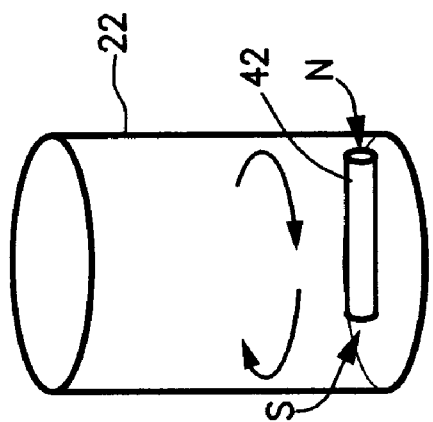

A magnetic stir element 42 of the type shown in FIGS. 6 and 6A is used with another embodiment of the method of the present invention. The magnetic stir element is a dowel 42 in which the opposite ends thereof are oppositely polarized and the dowel 40 is shorter than the internal diameter of the vessel 22. As the magnetic flux lines are rotated horizontally through 360 degrees, the dowel 42 continuously revolves around the vertical axis of the vessel 22 and while so revolving one end of the dowel 42 laterally tumbles against the sidewall of the vessel 22.

Figure 7:
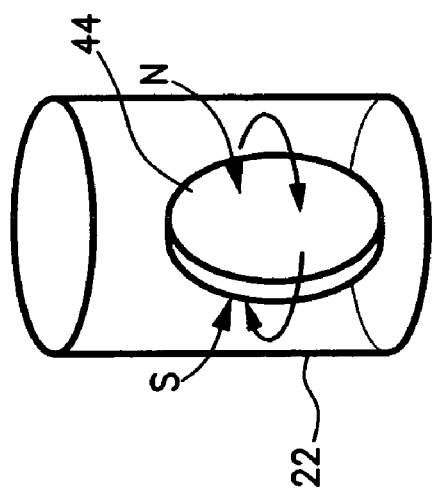
FIG. 7 illustrates still another type of magnetic stir element within a vessel.

A magnetic stir element 44 of the type shown in FIG. 7 is used with still another embodiment of the method of the present invention. The magnetic stir element is a disk 44 in which the opposite sides thereof are oppositely polarized. Preferably, the diameter of the disk 44 is more than or less than the internal diameter of the vessel 22. As the magnetic flux lines are rotated horizontally through 360 degrees, the disk 42 continuously revolves around the vertical axis of the vessel 22 and while so revolving, one edge of the disk 44 laterally tumbles against the sidewall of the vessel 22.

The position of the stirring vortex is dependent upon the size and shape of the magnetic stir element. The smaller the stir element relative to the inside diameter of the vessel, the more "off-center" the vortex will be towards the side of the vessel closest to the source of the magnetic field. If the stir element is nearly the same size as the inside diameter of the vessel, the vortex will be in the center of the vessel.

Figure 8:
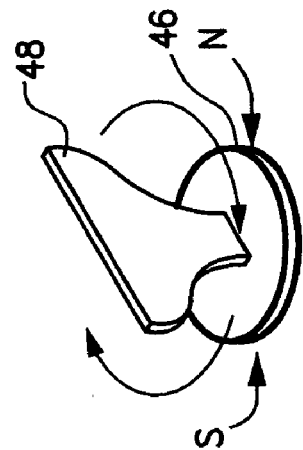
FIG. 8 illustrates yet another type of magnetic stir element.

A magnetic stir element 44 of the type shown in FIG. 8 is used with yet another embodiment of the method of the present invention. The magnetic stir element is a disk 46 having a fin 48 mounted on the disk 46. One side of the edge of the disk 46 is oppositely polarized from the opposite side of the edge of the disk. Preferably, the diameter of the disk 46 is less than the internal diameter of the vessel (not shown). As the magnetic flux lines are rotated horizontally through 360 degrees, the disk 48 continuously revolves around the vertical axis of the vessel and while so revolving one side of the edge of the disk 46 laterally tumbles against the sidewall of the vessel and the fin 48 stirs the contents of the vessel.

FIGS. 9A, 9B, 9C and 9D illustrate continuous lateral tumbling of magnetic stir elements 50 of the type illustrated in FIG. 5 or FIG. 6 as the magnetic flux lines are rotated in the horizontal plane through 360 degrees within the received vessels.

When the magnetic stir elements of the type illustrated in FIG. 7 are used, the orientation of the stir elements is 90 degrees from that shown for the stir elements 50 in FIGS. 9A, 9B, 9C and 9D In other various alternative embodiments (not shown):

(a) array-receiving sites are not provided at every angular position at a given height when the array-receiving sites are vertically disposed for receiving a plurality of the arrays at different heights and the array-receiving sites are also disposed about the vertical physical axis of the drive magnet for receiving a plurality of the arrays of vessels at different angular positions at at least one of the different heights;

(b) array-receiving sites are not provided at the same height in all of the vertical extensions of array-receiving sites when the array-receiving sites are vertically disposed for receiving a plurality of the arrays at different heights and the array-receiving sites are also disposed about the vertical physical axis of the drive magnet for receiving a plurality of the arrays of vessels at different angular positions at at least one of the different heights;

(c) the array-receiving sites are not vertically disposed for receiving a plurality of the arrays at different heights;

(d) the array-receiving sites are not disposed about the vertical physical axis of the drive magnet for receiving a plurality of the arrays of vessels at different angular positions at any given height;

(e) there is only one array-receiving site for receiving an array of vessels, wherein such array-receiving site is disposed to one side of a permanent magnet of the type and disposition shown in FIGS. 1, 2, 3 and 4;

(f) the array-receiving sites are within an assembly that is not rotatable.

In still other embodiments (not shown) the various aspects of the different embodiments described herein are combined with one another to the extent that they are not incompatible with each other.

The advantages specifically stated herein do not necessarily apply to every conceivable embodiment of the present invention. Further, such stated advantages of the present invention are only examples and should not be construed as the only advantages of the present invention. While the above description contains many specificities, these should not be construed as being necessarily required for use of the present invention or as limitations on the scope of the present invention, but rather as examples of the embodiments described herein. Other variations are possible and the scope of the present invention should be determined not by the embodiments described herein but rather by the claims and their legal equivalents.

The invention claimed is:

1. A system for mixing the contents of a two-dimensional array of vessels containing magnetic stir elements, wherein each vessel has a vertical axis as defined when the vessel is disposed for the mixing of said contents, the system comprising:

means for receiving at least one array of vessels in a disposition for the mixing of said contents;
a drive magnet for providing magnetic flux lines; and
means for causing the magnetic flux lines to rotate through 360 degrees;
wherein the drive magnet is disposed for causing the magnetic flux lines to rotate horizontally through 360 degrees within vessels received by the receiving means to thereby cause the magnetic stir elements in the received vessels to continuously revolve around the vertical axis of the vessel and while so revolving to continuously tumble laterally against the side wall of the vessel;
whereby the contents of a said vessel containing a said magnetic stir element are mixed by a vortex created by the continuous lateral tumbling of the stir element against the side wall of the vessel.

2. A system according to claim 1, wherein the receiving means includes a plurality of array-receiving sites that are vertically disposed at different heights in a direction that is parallel to a vertical physical axis of the drive magnet.

3. A system according to claim 2, wherein a physical axis of the drive magnet is elongated in said vertical plane to provide a vertically elongated zone of said horizontal magnetic flux lines; and wherein said vertically elongated zone substantially coincides with the vertical disposition of the array-receiving sites so that said magnetic flux lines are provided in arrays received at said different heights.

4. A system according to claim 3, wherein the receiving means includes a plurality of array-receiving sites that are horizontally disposed at least partially about the physical axis of the drive magnet at at least one of said different heights.

5. A system according to claim 2, wherein the receiving means includes a plurality of array-receiving sites that are horizontally disposed at least partially about the physical axis of the drive magnet at at least one of said different heights.

6. A system according to claim 5, wherein the receiving means comprises:

a plurality of shelves containing said plurality of vertically disposed array-receiving sites and said plurality of horizontally disposed array-receiving sites;
a plurality of poles that extend vertically through a plurality of apertures in said plurality of shelves; and
annular shelf-spacing elements for disposition about the poles between the shelves;
wherein the shelf-spacing elements can be so disposed that the space above one of said shelves can be different than the space above another of said shelves.

7. A system according to claim 5, wherein the receiving means are rotatable about the vertical physical axis of the drive magnet.

8. A system according to claim 7, further comprising:
means for maintaining the receiving means in one or another of a plurality of predetermined rotational positions when the receiving means is not being rotated by means coupled to the receiving means for rotating the receiving means.

9. A system according to claim 1, wherein the receiving means includes a plurality of array-receiving sites that are horizontally disposed at least partially about a vertical physical axis of the drive magnet.

10. A system according to claim 1, wherein the receiving means includes plurality of array-receiving sites that are vertically disposed at different heights.

11. A system according to claim 10, wherein the receiving means comprises:
- a plurality of shelves containing said plurality of vertically disposed array-receiving sites;
- a plurality of poles that extend vertically through a plurality of apertures in said plurality of shelves; and
- annular shelf-spacing elements for disposition about the poles above and/or between the shelves;
- wherein the shelf-spacing elements can be so disposed that the space above one of said shelves can be different than the space above another of said shelves.

12. A system according to claim 1, wherein the drive magnet is elongated in said vertical plane to provide a vertically elongated zone of horizontal magnetic flux lines; and
- wherein the means for causing the magnetic flux lines to rotate horizontally includes means for rotating the drive magnet about a vertical physical axis of rotation.

13. A system according to claim 1, wherein the drive magnet is disposed horizontally to one side of each array-receiving portion of the receiving means.

14. A method of mixing the contents of a two-dimensional array of vessels containing magnetic stir elements, wherein each vessel has a vertical axis as defined when the vessel is disposed for the mixing of said contents, the method comprising the steps of:
- (a) receiving at least one array of vessels in a disposition for the mixing of said contents; and
- (b) causing magnetic flux lines to rotate horizontally through 360 degrees within the received vessels to thereby cause the magnetic stir elements in the received vessels to continuously revolve around the vertical axis of the vessel and while so revolving to continuously tumble laterally against the side wall of the vessel;
- whereby the contents of a said vessel containing a said magnetic stir element are mixed by a vortex created by the continuous lateral tumbling of the stir element against the side wall of the vessel.

15. A method according to claim 14, wherein step (a) comprises the step of:
- (c) receiving a plurality of the arrays of vessels at a plurality of array-receiving sites that are vertically disposed at different heights in a direction that is parallel to a vertical physical axis of a drive magnet that provides said flux lines.

16. A method according to claim 15, wherein step (b) comprises the step of:
- (c) providing said flux lines within a vertically elongated zone of said horizontal magnetic flux lines that substantially coincides with the vertical disposition of the array-receiving sites to thereby provide said horizontally rotating magnetic flux lines in said plurality of said arrays received at said different heights 17. A method according to claim 16, wherein step (a) comprises the step of:
- (c) receiving a plurality of the arrays of vessels at a plurality of array-receiving sites that are horizontally disposed at least partially about a vertical physical axis of the drive magnet.

18. A method according to claim 15, wherein step (a) comprises the step of:
- (c) receiving a plurality of the arrays of vessels at a plurality of sites that are horizontally disposed at least partially about a vertical physical axis of the drive magnet.

19. A method according to claim 18, wherein step (a) comprises the step of:
- (c) rotating an assembly for receiving the arrays of vessels about the vertical physical axis of the drive magnet so that a plurality of said arrays of vessels can be received respectively at said different heights from a given rotational position.

20. A method according to claim 19, further comprising the step of:
- (d) maintaining said receiving assembly in one or another of a plurality of predetermined rotational positions when said receiving assembly is not being rotated by means coupled to the receiving assembly for rotating the receiving assembly.

21. A method according to claim 14, wherein step (a) comprises the step of:
- (c) receiving a plurality of the arrays of vessels at a plurality of array-receiving sites that are horizontally disposed at least partially about a vertical physical axis of a drive magnet that provides said flux lines.

22. A method according to claim 14, wherein step (a) comprises the step of:
- (c) receiving a plurality of the arrays of vessels at a plurality of array-receiving sites that are vertically disposed at different heights.

23. A method according to claim 14, wherein step (b) comprises the step of:
- (c) rotating a drive magnet that provides said flux lines about a vertical physical axis of rotation.

* * * * *